United States Patent [19]

Emanuel et al.

[11] Patent Number: 4,558,127
[45] Date of Patent: Dec. 10, 1985

[54] 5-FLUOROURACIL NITROXYL DERIVATIVES POSSESSING ANTITUMOR ACTIVITY

[76] Inventors: Nikolai M. Emanuel, ulitsa Kosygina, 6, kv. 44, Moscow; Albina N. Rozenberg, Shkoln bulvar, 7, kv. 97, Moskovskaya oblast, p.o. Chernogolovka; Valery A. Golubev, Institutsky prospekt, 6, kv. 115, Moskovskaya oblast, p.o. Chernogolovka; Gennady N. Bogdanov, ulitsa Pervaya, 19/1, kv. 11, Moskovskaya oblast, p.o. Chernogolovka; Ljubov S. Vasilieva, ulitsa Tsentralnaya, 4, kv. 9, Moskovskaya oblast, p.o. Chernogolovka; Nina P. Konovalova, ulitsa Dmitria Ulyanova, 4, korpus 2, kv. 339, Moscow, all of U.S.S.R.

[21] Appl. No.: 666,623
[22] PCT Filed: Mar. 7, 1984
[86] PCT No.: PCT/SU84/00013
§ 371 Date: Oct. 17, 1984
§ 102(e) Date: Oct. 17, 1984
[87] PCT Pub. No.: WO84/03510
PCT Pub. Date: Sep. 13, 1984
[51] Int. Cl.$^4$ .................. C07D 239/10; C07D 207/20
[52] U.S. Cl. ...................................... 544/310; 548/530
[58] Field of Search ................ 544/310; 514/269, 274; 548/530

[56] References Cited

U.S. PATENT DOCUMENTS

| | | | |
|---|---|---|---|
| 3,971,784 | 7/1976 | Tada | 544/310 |
| 4,130,648 | 12/1978 | Kijima et al. | 544/310 |
| 4,169,201 | 9/1979 | Kiss | 544/310 |
| 4,399,140 | 8/1983 | Gacek et al. | 544/316 |
| 4,415,573 | 11/1983 | Ochi et al. | 544/312 |

FOREIGN PATENT DOCUMENTS

| | | | |
|---|---|---|---|
| 53-87371 | 8/1978 | Japan | 544/310 |
| 59-1498 | 1/1984 | Japan | 544/310 |
| 1168391 | 10/1969 | United Kingdom | |
| 721439 | 3/1980 | U.S.S.R. | |

OTHER PUBLICATIONS

Donze et al., *Chemical Abstracts* 92: 43272g, (1980).

*Primary Examiner*—Donald G. Daus
*Assistant Examiner*—Stephen M. Kapner
*Attorney, Agent, or Firm*—Ladas & Parry

[57] ABSTRACT

5-Fluorouracil nitroxyl derivatives of the general formula:

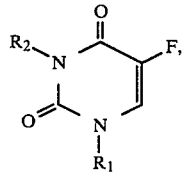

wherein
$R_1 = R_2 = X$,

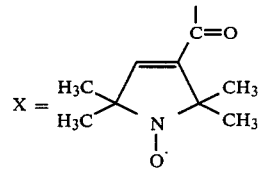

or $R_1 = X$, $R_2 = H$,
or $R_1 = H$, $R_2 = X$,
or $R_1 = Na$, $R_2 = X$, possessing an antitumor activity.

1 Claim, 2 Drawing Figures

5-FLUOROURACIL NITROXYL DERIVATIVES POSSESSING ANTITUMOR ACTIVITY

FIELD OF THE INVENTION

The present invention relates to novel biologically acitve compounds, viz. uracyl derivatives possessing antitumor activity.

BACKGROUND OF THE INVENTION

Known in the art is 5-fluorouracyl which is currently employed in oncology for non-operable forms of gastro-intestinal carcinoma, lung cancer and ovary carcinoma. (J. Amer. Chem. Soc. vol. 79, No. 16, published 1957; R. Dushinsky, E. Pleven, C. Heidelberg "The synthesis of 5-Fluoropyrimidines".

This compound, however, is highly toxic, it strongly affects the function of bone marrow and gastro-intestinal tract.

Another analog of the compound according to the present invention is 1-($\alpha$-furanidyl)-5-fluorouracyl (Ftorafur) (cf. British Pat. No. 1,168,391, Cl. C 07 d 51/30 1969). This is a low-toxic ($LD_{50}$ for mice is 750 mg/kg) compound having rather high activity in respect of solid experimental tumors: sarcoma 180, Harding-Passey melanoma, Walker carcinosarcoma, alveolar carcinoma of liver. In clinics the preparation based on Ftorafur is employed for treating mammal carcinoma, rectum carcinoma, large intestine and stomach cancer. This preparation, however, inhibits hemopoiesis and causes complications on the side of the gastro-intestinal tract. Furthermore, Ftorafur, likewise fluorouracyl, lacks paramagnetic properties.

DISCLOSURE OF THE INVENTION

The present invention is directed to the provision of novel compounds possessing an antitumor activity, a low toxicity and having paramagnetic properties.

This object is accomplished by nitroxyl derivatives of 5-fluorouracyl of the general formula:

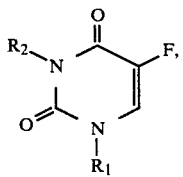

wherein
$R_1 = R_2 = X$,

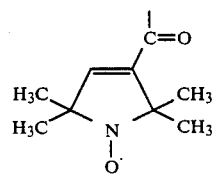

or $R_1 = X$, $R_2 = H$
or $R_1 = H$, $R_2 = X$,
or $R_1 = Na$, $R_2 = X$,
possessing antitumor activity.

These compounds feature a high antitumor activity which is by 2–4 times superior to that of Ftorafur and is comparable with the antitumor activity of 5-fluorouracyl.

The compounds according to the present invention are distinguished by their low toxicity, thus making it possible to minimize the undesirable side effects, enhance the effectiveness of inhibition of malignant neoplasms in the organism and to considerably enlarge the therapeutic scope of their action.

The availability of paramagnetic properties in the compounds according to the present invention enable a simplified control of the treatment process. The possibility of determination of paramagnetic preparations in the tumor tissues and spots of their localization up to the cellular level makes these compounds indispensible in the investigation of tumor processes and finding-out the mechanism of action of antitumor compounds.

BRIEF DESCRIPTION OF DRAWINGS

The present invention is further illustrated by specific embodiments thereof with reference to the accompanying drawings wherein.

BEST MODE OF CARRYING-OUT THE INVENTION

Figure 1:
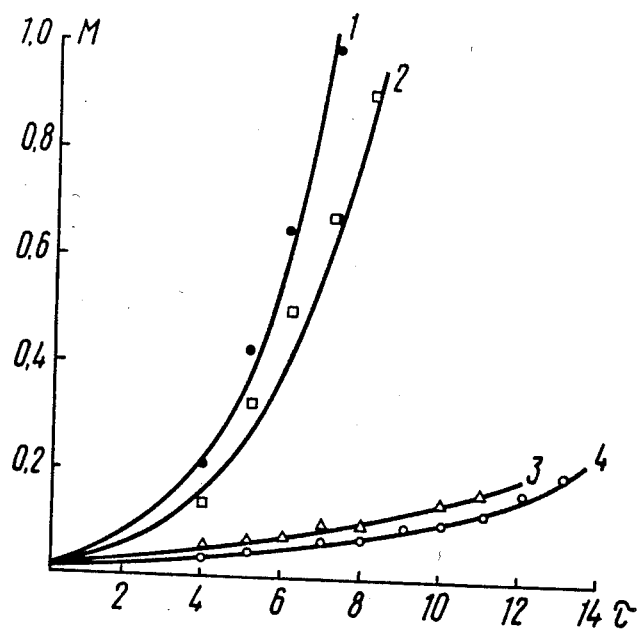
FIG. 1 shows kinetic curves of variation of mass of mice spleen in the case of La-leukemia in the control and upon administration of equimolar doses of Ftorafur, 5-fluorouracyl and a nitroxyl derivative of 5-fluorouracyl ($R_1 = Na$, $R_2 = X$) plotted in coordinates M- $\tau$, where M is mass of mice spleen in g, $\tau$-time, days.

The nitroxyl derivatives of 5-fluorouracyl according to the present invention corresponding to the above general formula, wherein $R_1 = R_2 = X$ or $R_1 = X$, $R_2 = H$ are prepared by condensation of bis-(trimethylsilyl)-5-fluorouracyl (A) with 2,2,5,5-tetramethyl-1-oxyl-$\Delta^3$-pyrrolin-3-carboxylic acid chloride (B) in a medium of an inert solvent such as benzene or without solvent at room temperature or upon a mild heating. At a molar ratio of compound (A) to compound (B) equal to 1:2–3 respectively 1,3-bis-(2,2,5,5-tetramethyl-1-oxyl-$\Delta^3$-pyrrolin-3-oyl)-5-fluorouracyl ($R_1 = R_2 = X$) is obtained. At a molar ratio of (A) to (B) equal to 2–3:1 respectively 1-(2,2,5,5-tetramethyl-1-oxyl-$\Delta^3$-pyrrolin-3-oyl)-5-fluorouracyl ($R_1 = X$, $R_2 = H$) is obtained.

The compound according to the present invention of the above-mentioned general formula, wherein $R_1 = H$, $R_2 = X$, namely sodium salt of 3-(2,2,5,5-tetramethyl-1-oxyl-$\Delta^3$-pyrrolin-3-oyl)-5-fluorouracyl is prepared by treating an alcoholic solution of 1,3-bis-(2,2,5,5-tetramethyl-1-oxyl-$\Delta^3$-pyrrolin-3-oyl)-5-fluorouracyl with an equivalent amount of sodium alcoholate.

The compound according to the present invention of the above-mentioned general formula, wherein $R_1 = H$, $R_2 = X$, namely 3-(2,2,5,5-tetramethyl-1-oxyl-$\Delta^3$-pyrrolin-3-oyl)-5-fluorouracyl is obtained by treating sodium salt of 3-(2,2,5,5-tetramethyl-1-oxyl- $\Delta^3$-pyrrolin-3-oyl)-5-fluorouracyl with an equivalent amount of a diluted acid, for example hydrochloric acid or sulphuric acid.

The following denotions of the compounds according to the present invention will be used hereinafter through the text of the specification:

(I)—a compound, wherein $R_1=R_2=X$;
(II)—a compound, wherein $R_1=X$, $R_2=H$;
(III)—a compound, wherein $R_1=H$, $R_2=X$;
(IV)—a compound, wherein $R_1=Na$, $R_2=X$.

The structure of the nitroxyl derivatives of 5-fluorouracyl according to the present invention is justified by way of elemental analysis and methods of EPR, IR, electron- and mass-spectrometry.

In IR-spectra of the compounds according to the present invention (I, II, III) a group of bands is observed within the range of 1,670–1,760 cm$^{-1}$ caused by vibrations of carbonyl groups of uracyl and pyrrolinoyl substituents. In accordance with the number of carbonyl groups the compounds according to the present invention (II, III, IV) contain a lesser number of carbonyl bands as compared to compound (I). In compound (IV) carbonyl bands of uracyl (1,561 and 1,673 cm$^{-1}$) are strongly shifted towards the low-frequency side as a result of delocalization of the negative charge of the anion onto carbonyl groups of uracyl.

In IR-spectra of all of the compounds according to the present invention (I, II, III, IV) also present are bands of stretching vibrations of C=C bonds of uracyl and pyrrolyine with a frequency of 1,620–1,625 cm$^{-1}$, bands of stretching vibrations of protons of methyl groups of pyrroline (2,800–3,000 cm$^{-1}$) and H—C=C groups of pyrroline and uracyl (3,030–3,100 cm$^{-1}$). In the compounds of and present invention (II, III) there are also bands of NH group with the frequency of 3,200 cm$^{-1}$.

Paramagnetism of the nitroxyl derivatives of 5-fluorouracyl according to the present invention has been verified by the EPR method. EPR spectra of diluted solutions of compounds (II, III, IV) consist of three lines characteristic for nitroxyl monoradicals. EPR spectra of compound (I) consist of nine lines and are characteristic for nitroxyl biradicals with the energy of the exchange interaction of electrons is equal to 1.8 $aN^{14}$. Constants of hyperfine interaction $aN^{14}$ and g-factors of the compounds according to the present invention (I, II, III, IV) are characteristic for nitroxyl radicals of the pyrrolin series.

Electron spectra of acetonitrile solutions of the nitroxyl derivatives of 5-fluorouracyl according to the present invention have four overlapping bands within the range of 12,500 to 50,000 cm$^{-1}$ which are due to absorption of nitroxyl, pyrroline and uracyl chromophores. The intensity of these bands in compound (I) is by 1.5–2 times higher than that of compounds (II and III). Electron spectra of aqueous solutions of compounds (II, III, IV) depend on pH. At a pH value of below or equal to 3 they are caused mainly by absorption of compounds (II or III) while at a pH above 11—by absorption of corresponding anions.

Electron spectra of compound (III) and its respective anion are significantly different in both frequency and intensity of the band associated with absorption of uracyl chromophore. In the above-specified compound this band has the frequency of 41,470 cm$^{-1}$, in the anion—33,710 cm$^{-1}$. Such difference of frequencies is characteristics for all 3-substituted uracyls, thus proving the structure of compounds (III and IV). Spectra of compound (II) and its respective anion are similar to one another which is also typical for 1-substituted uracyls.

In mass-spectra of compounds (I, II, III) molecular ions M+ are present, as well as fragmental ions justifying the number and point of attachment of pyrrolinoyl groups X to 5-fluorourcyl denoted hereinafter as Fu. Thus, in the mass-spectrum of compound (III) there are fragmental ions m/e 167 [X]+ and m/e 130 [Fu]+, as well as fragmental ions m/e 226 [XNCONH$_2$]+ and m/e 225 [XNHCONH]+ demonstrating the addition of 2,2,5,5,-tetramethyl-1-oxyl-$\Delta^3$-pyrrolinoyl group to the nitrogen atom of uracyl located between carbonyl groups. In the mass-spectrum of compound (I) there is a fragmental ion m/e 296 [XFu]+ caused by cleavage of one of two X groups from the molecular ion M+.

Unlike 5-fluorouracyl, compounds (I, II, III) are wellsoluble in organic solvents: alcohols, acetone, acetonitrile, dimethylformamide, dimethylsulphoxide. Compound (IV) is very well soluble in water. Its aqueous solutions have an alkaline reaction. Compounds (I, II, III) are sparingly soluble in water. However, compounds (II, III) are well soluble in aqueous solutions of alkalis or buffer solutions at a pH above 10.

Compounds (III, IV) are stable enough against hydrolysis. At room temperature at a pH within the range of from 3 to 11 they do not undergo any noticeable hydrolytical decomposition for a period of about 5 hours.

Compound (II) in aqueous solutions of alkalis gets rapidly hydrolyzed to fluorouracyl and 2,2,5,5-tetramethyl-1-oxyl-$\Delta^3$-pyrrolin-3-carboxylic acid. The rate of hydrolysis is increased with increasing pH of the reaction medium.

Given hereinbelow are examples illustrating preparation of nitroxyl derivatives of 5-fluorouracyl, as well as physical and spectroscopic characteristics of the prepared compounds.

EXAMPLE 1

Preparation of 1,3-bis-(2,2,5,5-tetramethyl-1-oxyl-$\Delta^3$-pyrrolin-3-oyl)-5-fluorouracyl (compound I)

To a solution of 8.11 g of 2,2,5,5-tetramethyl-1-oxyl-$\Delta^3$-pyrrolin-3-carboxylic acid chloride in 40 ml of dry benzene 5.49 g of bis-(trimethylsilyl)-5-fluorouracyl are added in the atmosphere of dry nitrogen. Precipitated orange crystals of compound (I) are filtered-off, washed with a small amount of benzene and hexane and dried to give 7.1 g (77% as calculated for the employed bis-/trimethylsilyl/-5-fluorouracyl) of the product.

The thus-prepared compound is recrystallized from toluene to give orange prism-like crystals melting at 195°–198° C.

Found, %: C 57.4±0.3; H 5.9±0.1; N 12.1±0.1; F 3.7±0.3; m/e 462 [M]+. $C_{22}H_{27}FN_4O_6$. Calculated, %: C 57.14; H 5.98; N 12.11; F 4.11.

Molecular mass 462.4745.

IR spectrum in CCl$_4$, $\nu$, cm$^{-1}$ ($\epsilon$,1/mol.cm): 1,621 (230) C=C; 1,676 (620); 1,705 (1,100); 1,729 (800); 1,762 (520); C=O; 2,870 (100); 2,935 (220); 2,984 (310) CH$_3$; 3,030 (80), 3,065 (70), 3,095 (90) CH.

EPR spectrum in toluene at 25° C. and concentration of the resulting compound of $5\times10^{-4}$ mol/l consists of 9 lines with the ratio of amplitudes of 0.16:100:29:33:95:32:24:86:0.15 and distances of lateral lines to the central one equal to 0.41; 0.58; 1; 2.23; g-factor=2.0056±1×10$^{-5}$; $aN^{14}$=14.18±0.04 Gs.

Electron spectrum in acetonitrile, $\nu_{max}$, cm$^{-1}$ ($\epsilon$, 1/mol.cm): 26,500±100 (81±2), 37,400±100 (8,200±100), 44,560±60 (20,900±200), 47,000±100 (22,400±200).

Mass-spectrum m/e [ion] (I/I$_{max}$, %): 463 [M+I]+ (1.4); 462 M+(4.4); 447 [M—CH$_3$]+ (0.22); 432

[M—NO]+ (2.2); 296 [XFu]+ (5.7); 281 [X Fu—CH$_3$]+ (0.16); 266 [X Fu—NO]+ (4.7); 167 [X]+ (16); 152 [X—CH$_3$]+ (16); 139 [X—CO]+; 137 [X—NO]+ (52); 109 [X—NOCO]+ (100), wherein X and Fu are as indentified above.

EXAMPLE 2

Preparation of 1-(2,2,5,5-tetramethyl-1-oxyl-Δ$^3$pyrrolin-3-oyl)-5-fluorouracyl (compound II)

To a solution of 2.02 g of 2,2,5,5-tetramethyl-1-oxyl-Δ$^3$-pyrrolin-3-carboxylic acid chloride in 100 ml of dry benzene 5.49 g of bis-(trimethylsilyl)-5-fluorouracyl are added in the atmosphere of dry nitrogen. Orange-red crystals of compound (II) are filtered-off, washed with benzene and then with hexane and dried to give 1.5 g (50% as calculated for 2,2,5,5-tetramethyl-1-oxyl-Δ$^3$-pyrrolin-3-carboxylic acid chloride) of the product.

The resulting compound is recrystallized from nitromethane to obtain orange-red needle-like crystals melting at 198°–201° C.

Found, %: C 52.4±0.3; H 5.10±0.05; N 13.8±0.2; m/e 296 [M]+ C$_{13}$H$_{15}$FN$_3$O$_4$. Calculated, %: C 52.70; H 5.10; N 14.18.

Molecular mass is 296.2760.

IR Spectrum in acetonitrile, ν, cm$^{-1}$ (ϵ, 1/mol.cm): 1.627 (110) C=C; 1.685 (330), 1,730 (1,700) C=O; 2,835 (40), 2,872 (52), 2,946 (155), 2,983 (210) CH$_3$; 3,105 (140) CH; 3,225 (130) NH.

EPR spectrum in toluene at 25° C. and concentration of the resulting compound of 5×10$^{-4}$ mol/l consists of 3 lines with the ratio of amplitudes: 100:99:9; g=2.00562±3×10$^{-5}$; aN$^{14}$=14.25±0.03 Gs.

Electron spectrum in acetonitrile, ν$_{max}$, cm$^{-1}$ (ϵ, 1/mol.cm): 26,120±50 (50±1), 37,120±50 (7,700±100), 40,700±40 (10,000±100), 47030±40 (13,400±200).

Electron spectrum in 0.001 M aqueous solution of hydrochloric acid, μ$_{max}$, cm$^{-1}$ (ϵ, 1mol.cm): 41,840±80 (9,700), 47,320±80 (≦14,400).

EXAMPLE 3

Preparation of sodium salt of 3-(2,2,5,5-tetramethyl-1-oxyl-Δ$^3$-pyrrolin-3-oyl)-5-fluorouracyl (compound IV)

To 4.62 g of 1,3-bis-(2,2,5,5-tetramethyl-1-oxyl-Δ$^3$-pyrrolin-3-oyl)-5-fluorouracyl (compound I) 10 ml of a 1 M solution of sodium ethylate in absolute ethanol are added.

The reaction mixture is stirred, then added with 40 ml of diethyl ether. The resulting yellow precipitate of the salt is filtered-off, washed with diethyl ether and dried. The yield is 3.05 g (96%). The salt has no clear-cut melting point, it gradually decomposes at a temperature within the range of from 250° to 330° C.

Found, %: N 13.0±0.2. C$_{13}$H$_{14}$FN$_3$O$_4$Na. Calculated, %: N 13.20.

IR spectrum in vaseline oil, ν, cm$^{-1}$: 1,620 C=C; 1,561; 1,673; 1,738 C=O; 3,070 CH.

Electron spectrum in 0.001 M aqueous solution of hydrochloric acid, ν$_{max}$, cm$^{-1}$ (ϵ, 1/mol.cm): 37,400±50 (7,200±100), 41.700±40 (13.000±100), 46,700±100 (12,100±100).

Electron spectrum in 0.001 M aqueous solution of sodium hydroxide, ν$_{max}$, cm$^{-1}$ (ϵ, 1/mol.cm): 33,700±30 (8,100±100), 44,270±50 (15,700±300).

EPR spectrum in water at 25° C. and concentration of the resulting salt of 5×10$^{-4}$ mol/l consists of three lines with the ratio of amplitudes: 100:101:80; g=2.00514±1×10$^{-5}$, aN$^{14}$=15.88±0.05 Gs.

EXAMPLE 4

Preparation of 3-(2,2,5,5-tetramethyl-1-oxyl-Δ$^3$-pyrrolin-3-oyl)-5-fluoracyl (compound III).

To 1.59 g of sodium salt of 3-(2,2,5,5-tetramethyl-1-oxyl-Δ$^3$-pyrrolin-3-oyl)-5-fluororacyl (compound IV) 25 ml of a 0.2N aqueous solution of hydrochloric acid are added. The mixture is stirred for 10 minutes and extracted for several times with chloroform. Chloroform extracts are dried with Na$_2$SO$_4$, the solvent is evaporated in vacuum and the residue is recrystallized from toluene. A compound thus obtained is in the form of fine yellow needles melting at 169°–171° C. The yield is 1.11 g (75%).

Found, %: C 52.6±0.2; H 5.09±0.05; N 14.3±0.1; F 6.44±0.05; m/e 296 [M]+. C$_{13}$H$_{15}$FN$_3$O$_4$. Calculated, %: C 52.70; H 5.10; N 14.18; F 6.41.

Molecular mass 296.276.

IR spectrum in acetonitrile, ν, cm$^{-1}$ (ϵ, 1/mol.cm): 1,622 (180) C=C; 1,680 (1.330), 1.723 (760), 1,754 (960) C=O; 2,877 (47); 2,940 (130); 2,989 (190) CH$_3$; 3,087 (90) CH; 3,270 (140) NH.

EPR spectrum in toluene at 25° C. and concentration of the resulting compound of 5×10$^{-4}$ mol/l consists of 3 lines with the ratio of amplitudes of 100:99:90; g=2.00561±1×10$^{-5}$; aN$^{14}$=14.15±0.01 Gs.

Electron spectrum in acetonitrile, ν$_{max}$, cm$^{-1}$ (ϵ, 1/mol.cm): 25,140±20 (52.6±0.5), 38,190±20 (8,500±200), 42,460±20 (14,000±500), 47430±60 (13,200±600).

Electron spectrum in 0.001 M aqueous solution of hydrochloric acid, ν$_{max}$, cm$^{-1}$ (ϵ, 1/mol.cm): 37,410±60 (7,200±100) 41,710±30 (13,900±100); 46,700±70 (12,000±100).

Electron spectrum in 0.001 M aqueous solution of sodium hydroxide, ν$_{max}$, cm$^{-1}$ (ϵ, 1/mol.cm): 33,710±30 (8,160±150), 44,270±90 (15,700±300).

Mass-spectrum, m/e [ion] (I/I$_{max}$, %): 297 [M+1]+ (7.1); 296 [M]+ (23); 282 [HM—CH$_3$]+ (26); 281 [M—CH$_3$]+ (1.2); 266[M-NO]+ (12); 1226 [XNH CO NH$_2$]+ (0.44); 225 [XNHCONH]+ (1,4); 167 [X]+ (42); 152 [X—CH$_3$]+ (67); 139 [X—CO]+ (16); 137 [X—NO]+ (82); 136 [X—HNO]+ (100); 130 [Fu]+ (91); 109 [X—NOCO]+ (96), wherein X and Fu are as identified above.

The nitroxyl derivatives of 5-fluorouracyl according to the present invention have been subjected to comparative tests using 5-fluorouracyl and Ftorafur for the comparison purposes. The results of these tests are shown in the Table hereinbelow.

Toxicity of the compounds according to the present invention has been determined on mongrel white mice in experimental intraperitoneal administration of these compounds and evaluated by the Burns method (using curves of accumulation of the animal death frequencies vs. dose).

As the toxicity characteristic use was made of the dose causing death of 50% of the animals employed for the experiment (LD$_{50}$).

For the determination of toxicity of (1,3-bis-(2,2,5,5-tetramethyl-1-oxyl-Δ$^3$-pyrrolin-3-oyl)-5-fluorouracyl(-compound I), 1-(2,2,5,5-tetramethyl-1-oxyl-Δ$^3$-pyrrolin-3-oyl)-5-fluorouracyl (compound II) and 3-(2,2,5,5-tetramethyl-1-oxyl-Δ$^3$-pyrrolin-3-oyl)-5-fluorouracyl (compound III), these compounds were administered intraperitoneally in the form of an emulsion in a 10% aqueous solution of polyoxyethylsorbitan monooleate (Tween-80, Ferak Berlin West Germany).

For the determination of toxicity of sodium salt of 3-(2,2,5,5-tetramethyl-1-oxyl-Δ³-pyrrolin-3-oyl)-5-fluorouracyl (compound IV), Ftorafur and 5-fluorouracyl, these compounds were also administered intraperitoneally in the form of aqueous solutions.

The test results have shown that compound (I) is by 3.5 times less toxic than 5-fluorouracyl. Toxicity of compound (II) is substantially similar to that of 5-fluorouracyl. Compounds (III, IV) are by 5 times less toxic than 5-fluorouracyl and approach toxicity of Ftorafur.

For the determination of antitumor activity these compounds (I, II, III, IV), 5-fluorouracyl and Ftorafur were used in the same solvents as in the determination of toxicity.

The determination of antitumor activity was effected on grafted tumors of mice: leukemia L-1210, leukemia P-388, Leukemia La, melanoma B-16, adenocarcinoma 755 (Ca-755), as well as on grafted tumors of rats: Schwetz erythroleukosis, Walker carcinosarcoma (WCS), Geren carcinoma.

Leukemia L-1210 was grafted intraperitoneally, $10^5$ cells in 0.2 ml of ascitic liquid. Compound (IV) was also administered intraperitoneally on a daily basis, beginning with the 1-st day after grafting of the tumor. The treatment schedule is shown in the Table herereinbelow.

Leukemia P-388 was grafted intraperitoneally, $10^6$ cells in 0.2 ml of ascitic liquid. Compound (IV) was administered also intraperitoneally on a daily basis beginning with the 1-st day after grafting of the tumor. The treatment schedule is also given in the Table hereinbelow.

Leukemia La was grafted intraperitoneally using a suspension of leukemic cells in a physiological solution. The inoculum contained $10^8$ of leukemia cells. Compounds (I, II, III, IV), 5-fluorouracyl and Ftorafur were also administered intraperitoneally, the first administration was effected 3 hours after grafting of the tumor and then—daily. The treatment schedule is shown in the Table hereinbelow.

Solid tumors (molanoma B-16, adenocarcinoma 755, Schwetz erythroleukosis, Walker carcinosarcoma, Geren carcinoma) were grafted using a tumor cell suspension in a physiological solution (dilution of 1:1 by mass) and were hypodermally administered in the dose of 0.3 ml to each test animal. The test compounds were administered intraperitoneally starting from the 1-st day after grafting of the tumor in the case of melanoma B-16, adenocarcinoma 755, Walker carcinosarcoma or after 7 days—in the case of grafting of Schwetz erythroleukosis and Geren carcinoma. The treatment schedule is shown in the Table hereinbelow.

In the determination of the antitumor activity the test compounds were introduced in equitoxic doses. Ftorafur was also used in the optimal dose which is equal to 300 mg/g.

The criterion of the antitumor activity for leukemia P-338, L-1210 and La is the extension of an average life span (ELS) of the test animals as compared to the control ones, expressed in percent and calculated by the formula:

$$ELS = \frac{100 \cdot (L_t - L_c)}{L_c}$$

wherein $L_t$—life span of animals in the test group;
$L_c$—life span of animals in the control group, i.e. without administration of the test compounds.

As the criterion of antitumor activity on solid tumors used is the inhibition (I) of the tumor volume gain in comparison with the control, expressed in percent and calculated by the formula:

$$I = \frac{100 \cdot (V_c - V_t)}{V_c}$$

wherein $V_c$—average volume of the tumor in the control,
$V_t$—average volume of the tumor in the experiment.

In the case of leukemia La and adencocarcinoma 755 the Table shows one more criterion of the antitumor activity, notably the kinetic criterion $\mathcal{X} = 1 - \phi_t/\phi_c$, wherein $\phi_t$ and $\phi_c$ are tumor growth rates in the test and control respectively.

The comparative assessment of the scope of therapeutic action is effected using chemotherapeutic indices $I_{40}$, $I_{60}$ and $I_{100}$: $I_{40}=LD_{10}/ED_{40}$, $I_{60}=LD_{10}/ED_{60}$ $I_{100}=LD_{10}/ED_{100}$, where $LD_{10}$=dose causing death of 10% of the animals; $ED_{40}$, $ED_{60}$ and $ED_{100}$ are effective doses causing extension of the animal's life span by 40, 60 and 100 percent respectively.

TABLE

| Test compound 1 | Animals Line 2 | num- ber 3 | Toxi- city, LD$_{50}$, mg/kg 4 | Tumor 5 | Mode of graft- ing 6 | Control, life span, days 7 | Single dose, mg/kg 8 | Treatment schedule, days after grafting of the tumor 9 | Antimor activity χ 10 | Inhibi- tion, % 11 | ELS, % 12 | Che- mother- apeu- tic index 13 |
|---|---|---|---|---|---|---|---|---|---|---|---|---|
| I | Mice C57Bl | 20 | 350 | La | i/p | 6,5 | 75 | 1-7 | 0,1 | — | 30 | $I_{40} = 4,0$ |
| I | Mice CBAF$_1$ | 20 | — | B-16 | h/d | — | 75 | 1-10 | — | 15 | — | — |
| II | Mice C57Bl | 20 | 150 | La | i/p | 6,5 | 75 | 1-7 | 0.5 | — | 45 | $I_{40} = 2,0$ |
| III | Mice C57Bl | 20 | 550 | La | i/p | 6,5 | 65 | 1-7 | 0,2 | — | 40 | $I_{40} = 7,8$ |
| IV | Mice BDF$_1$ | 20 | 510 | L-1210 | i/p | 7,5 | 65 | 1-9 | — | — | 100 | — |
| IV | Mice | 20 | — | L-1210 | i/p | 7,5 | 75 | 1-7 | — | — | 60 | $I_{60} = 5,6$ |

TABLE-continued

| Test compound 1 | Animals Line 2 | Animals number 3 | Toxicity, LD$_{50}$, mg/kg 4 | Tumor 5 | Mode of grafting 6 | Control, life span, days 7 | Single dose, mg/kg 8 | Treatment schedule, days after grafting of the tumor 9 | Antimor activity $\chi$ 10 | Antimor activity Inhibition, % 11 | Antimor activity ELS, % 12 | Chemotherapeutic index 13 |
|---|---|---|---|---|---|---|---|---|---|---|---|---|
| IV | Mice BDF$_1$ | 20 | — | P-388 | i/p | 10 | 75 | 1-7 | — | — | 90 | — |
| IV | Mice BDF$_1$ | 20 | — | P-388 | i/p | 10 | 100 | 1,3,5,7,9 | — | — | 100 | $I_{100} = 4.2$ |
| IV | Mice BDF$_1$ | 20 | — | La | i/p | 6,5 | 75 | 1-7 | 0.7 | — | 80 | — |
| IV | Mice C57Bl | 20 | — | La | i/p | 6,5 | 100 | 1,3,5,7,9 | — | — | 60 | $I_{60} = 4.2$ |
| IV | Mice C57Bl | 20 | — | B-16 | h/d | — | 75 | 1-10 | — | 30 | — | — |
| IV | Mice CBAF$_1$ | 20 | — | Ca-755 | h/d | — | 65 | 1-10 | 0.3 | 70 | — | — |
| IV | Mice C57Bl | 20 | — | WCS | h/d | — | 60 | 1-10 | — | 75 | — | — |
| IV | Rats mon | 20 | — | Schwetz erythroleukosis | h/d | — | 75 | 7-14 | — | 45 | — | — |
| IV | Rats mon. | 20 | — | Geren carcinoma | h/d | — | 60 | 7-16 | — | 20 | — | — |
| 5-fluorouracyl | Mice C57Bl | 20 | 100 | La | i/p | 6.5 | 25 | 1-7 | — | — | 57 | $I_{60} = 3.6$ |
| 5-fluorouracyl | Mice C57Bl | 20 | — | La | i/p | 6,5 | 35 | 1,3,5,7 | 0.67 | — | 57 | — |
| 5-fluorouracyl | Mice CBAF$_1$ | 20 | — | B-16 | h/d | — | 25 | 1-10 | — | 0 | — | — |
| 5-fluorouracyl | Rats mon. | 20 | — | Schwetz erythroleukosis | h/d | — | 25 | 7-14 | — | 15 | — | — |
| Ftorafur | Mice C57Bl | 20 | 640 | La | i/p | — | 45 | 1-6 | 0.17 | — | 15 | — |
| Ftorafur | Mice C57Bl | 20 | — | La | i/p | — | 300 | 1,5,9 | — | — | 60 | $I_{60} = 2.0$ |
| Ftorafur | Mice CBAF$_1$ | 20 | — | B-16 | i/p | — | 300 | 1,5,9 | — | 10 | — | — |
| Ftorafur | Rats mon | 20 | — | Schwetz erythroleukosis | h/d | — | 90 | 7-14 | — | 15 | — | — |

Note:
[1] mon. - mongrel
[2] i/p - intraperitoneally
[3] h/d - hypodermally
[4] WCS - Walker carcinosarcoma As it is seen from the above Table, all of the compounds according to the present invention have a clearly pronounced antileukemic effect.

Thus, compound (I) in the case of leukemia La is by 2 times more effective than Ftorafur at similar schedules of treatment for Ftorafur as regards the ELS index; kinetic criteria $\mathcal{X}$ of both compounds have close values. Compound (I) is close to 5-fluorouracyl in its therapeutic effect on leukemia La.

In the case of leukemia La compound (II) is by 3 times more effective than Ftorafur as regards the characteristics of ELS and kinetic criterion and similar, in these characteristics, to 5-fluorouracyl.

In the case of leukemia La compound (III) is by 2 times more effective than Ftorafur as regards the characteristic of ELS, while kinetic criteria $\mathcal{X}$ of both compounds have close values. Compound (III), as regards its therapeutic effect on leukemia La, is close to 5-fluorouracyl.

The most active is compound (IV) which is superior, in respect of leukemia La, to Ftorafur by 5 times in the effectiveness of its action upon comparison of both compounds in equitoxic doses and comparable treatment schedules. The effectiveness of compound (IV) is comparable with that of 5-fluorouracyl.

Compound (IV) also shows a high antitumor activity in the case of leukemia L-1210 and leukemia P-388.

In respect of their effect on solid tumors, the most active out of the compounds according to the present invention is compound (IV). At comparable doses and treatment procedures compound (IV) is by 2-3 times more effective than Ftorafur and 5-fluororuracyl in the case of Schwetz erythroleukosis, by 3 times more effective than Ftirafur in the case of melanoma B-16 (5-fluorouracyl shows no activity upon the effect on melanoma B-16). Compound (IV) features a considerable antitumor activity in respect of adenocarcinoma 755 and Walker carcinosarcoma.

All the compounds according to the present invention feature high values of chemotherapeutic indices. Thus, in the case of leukemia La the chemotherapeutic index $I_{60}$ of compound (IV) is by 2 times higher as compared to the $I_{60}$ of Ftorafur and by 1.2 time as high as that of 5-fluorouracyl.

To reveal the antitumor activity and kinetic characteristics of the therapeutic effectiveness of compound (IV), Ftorafur and 5-fluorouracyl in the case of leukemia La, a series of experiments was conducted on mice C 57 B1. Leukemia La was grafted intraperitoneally by means of a suspension of leukemic cells in a physiological solution. The inoculum contained $10^8$ of leukemic cells. Compound (IV), Ftorafur and 5-fluorouracyl were also administered intraperitoneally so that the first administration was effected 3 hours after the tumor grafting, and then—on a daily basis over the period of seven days.

Determined were the variations of mass (M) of mice spleen in g over 14 days ($\tau$). The obtained data were used to plot a graph in coordinates M-$\tau$ represented in FIG. 1.

FIG. 1 shows kinetic curves of variation of mice spleen mass in the case of leukosis La in a control experiment (without administration of the test compound) and upon the effect of equimolar single doses (0.2 mmol/kg) of the test compounds: kinetic curve 1—for the control experiment, kinetic curve 2—for the effect of Ftorafur, kinetic curve 3—for the effect of 5-fluorouracyl, kinetic curve 4—for the effect of compound (IV).

The slope of kinetic curves of spleen mass gain shows that compound (IV) is the most effective in inhibition of leukemia La. Its activity is by several times superior to that of 5-fluorouracyl and by many times—to that of Ftorafur.

To reveal the antitumor activity and kinetic characteristic of the therapeutic effectiveness of compound (IV) and Ftorafur in the case of adenocarcinoma 755, a series of experiments was conducted on mice C 57 B1. Adenocarcinoma 755 was grafted using a tumor cell suspension in a physiological solution (dilution 1:1 by mass) and was administered hypodermally in the dose of 0.3 ml to each mouse. The test compounds were administered intraperitoneally, starting from the 1-st day after grafting of the tumor, daily over the period of 10 days.

The tumor volume increase (V) of adenocarcinoma 755 was determined in $cm^3$ for 28 days ($\tau$). Using the thus-obtained data, a graph was plotted in coordinated V-$\tau$ which is shown in FIG. 2.

Figure 2:
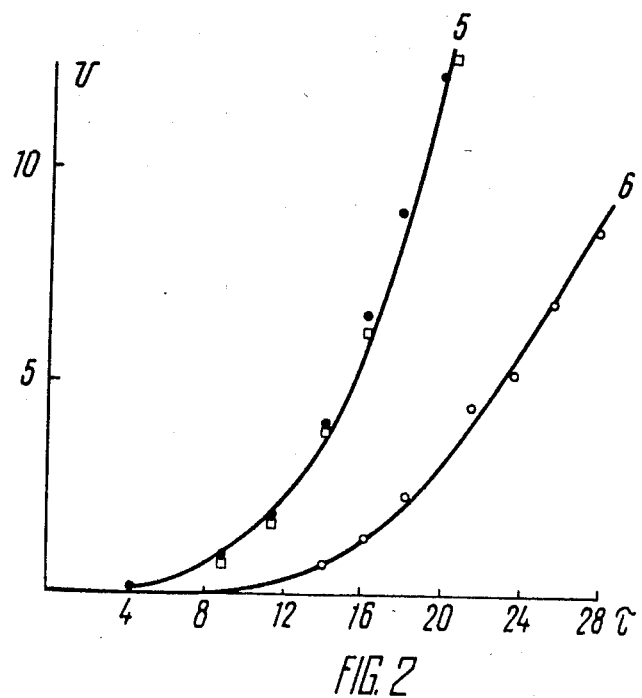
FIG. 2 shows kinetic curves of a tumor volume gain in the case of adenocarcinoma 755 in mice in the control and upon the administration of equimolar doses of Ftorafur and a nitroxyl derivative of 5-fluorouracyl ($R_1 = Na$, $R_2 = X$), plotted in coordinates V- $\tau$, where V is volume of adenocarcinoma 755 tumor, in $cm^3$, $\tau$-time, days.

FIG. 2 demonstrates kinetic curves of the tumor volume gain in the case of adenocarcinoma 755 in the control experiment (without administration of the test compound) and upon the action of equimolar single doses (0.2 mmol/kg) of the test compounds:

kinetic curve 5—for the control experiment and upon the effect of Ftorafur.

kinetic curve 6—for the effect of compound (IV).

In the kinetic curve 5 experimental points corresponding to the control experiment are conventionally shown as circles, while experimental points corresponding to the use of Ftorafur are conventionally shown as squares.

As it is seen in FIG. 2, compound (IV) ensures a considerable inhibition of the tumor growth, whereas Ftorafur provides no antitumor activity.

As it follows from the above-given test results, compound (IV) combines in itself the best property of 5-fluorouracyl—its high antileukemic activity with the best properties of Ftorafur—its low toxicity and a high antitumor activity in respect of solid tumors.

Industrial Applicability

The nitroxyl derivatives of 5-fluorouracyl according to the present invention possessing antitumor activity can be useful in biology and medicine.

We claim:

1. Nitroxyl compound of 5-fluorouracyl of the formula:

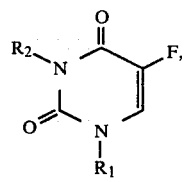

wherein
$R_1 = R_2 = X$,

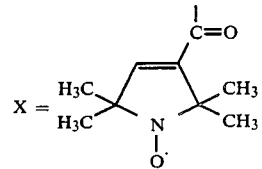

or $R_1 = X$, $R_2 = H$,
or $R_1 = H$, $R_2 = X$,
or $R_1 = Na$, $R_2 = X$,
possessing an antitumor activity.

* * * * *